United States Patent [19]

Ceriani et al.

[11] Patent Number: 5,077,220

[45] Date of Patent: Dec. 31, 1991

[54] MONOCLONAL ANTIBODY SPECIFIC TO A NOVEL GLYCOPROTEIN ANTIGEN ON HUMAN CARCINOMA CELLS

[75] Inventors: Roberto L. Ceriani; Jerry A. Peterson, both of Lafayette, Calif.

[73] Assignee: John Muir Cancer & Aging Institute, Walnut Creek, Calif.

[21] Appl. No.: 237,218

[22] Filed: Aug. 26, 1988

[51] Int. Cl.[5] ..................... C12Q 1/00; G01N 33/53; C12N 15/00; C12N 5/00

[52] U.S. Cl. ................... 435/7.23; 435/172.2; 435/240.27; 436/548; 530/387; 935/104

[58] Field of Search ............... 435/7, 172.2, 240.26, 435/240.27, 7.1, 7.23; 436/503, 518, 543, 547, 548, 800, 811, 813, 819; 530/387, 389, 812, 828, 832, 836, 809; 424/1.1, 3, 85.8; 935/89, 103, 104, 106, 107, 95

[56] References Cited

PUBLICATIONS

H. M. Geysen et al., Proc. Natl. Acad. Sci., 81: 3998–4002 (1984).
Griffiths, A. et al., Int Jour Cancer 40:319–327 (1987).
Burchell, J. et al., Jour Immunol. 131(1):508–513 (1983).
Gendler, S. et al., PNAS 84:6060–6064 (1987).
Arklie, J. et al., Biol Abstr. 73 (1982) #26174.
van Hell, H. et al., in "Alternative Immunoassays", (Collins, ed), Wiley & Sons, publ. 1985, pp. 39–58.

Primary Examiner—Esther L. Kepplinger
Assistant Examiner—Jacintha M. Stall
Attorney, Agent, or Firm—Myron C. Cass

[57] ABSTRACT

A hybridoma cell line is provided which is capable of producing monoclonal antibodies which bind to a unique determinant site on the surface and/or in the cytoplasm of human breast carcinoma cells and carcinoma cells of other adenocarcinomas and on the surface of normal human breast epithelial cells. The cell line of the invention was developed by immunizing mice with a select group of immunogens and a conventional myeloma cell line for fusion with the murine splenocytes harvested.

The monoclonal antibody is identified as the BrE2 monoclonal antibody. The antigen is characterized as a high molecular weight glycoprotein complex having a molecular exceeding 400,000 daltons. This monoclonal antibody is especially useful for diagnostic, prognostic and therapeutic applications in human breast cell carcinoma.

8 Claims, No Drawings

MONOCLONAL ANTIBODY SPECIFIC TO A NOVEL GLYCOPROTEIN ANTIGEN ON HUMAN CARCINOMA CELLS This invention was made with Government funding support under National Institutes of Health grant Nos. CA39931 and CA39932.

FIELD OF THE INVENTION

This invention relates to a monoclonal antibody which binds to antigens of human carcinomas and more particularly, relates to a monoclonal antibody which binds specifically to a mucin-like glycoprotein complex of very high molecular weight on the surface and/or in the cytoplasm of human breast carcinoma cells and carcinoma cells of other adenocarcinomas, and on the surface of normal human breast epithelial cells.

DESCRIPTION OF THE PRIOR ART

Monoclonal antibodies have been developed that recognize a high molecular weight mucin-like glycoprotein complex present on the surface of normal human breast epithelial cells. Peterson et al., Imperial Cancer Research Fund, London, England, Mar. 2-3 (1981); Taylor-Papadimitriou et al., Int. J. Cancer, 28:17-21 (1981); Ceriani et al., Somatic Cell Genetics, 9:415-427 (1983). Other investigators have developed monoclonal antibodies using both the human milk fat globule as the immunizing agent [Taylor-Papadimitriou et al., Int. J. Cancer, 28:17-21 (1981); Ceriani et al., Somatic Cell Genetics, 9:415-427 (1983)] and different breast tumor cells as the immunizing agents [Papsidero et al., Cancer Research, 43:1741-1747 (1983); Kufe et al., Hybridoma, 3:223-232 (1984); Frankel et al., J. Biol. Response Mod., 4:273-286 (1985); Colcher et al., Proc. Natl. Acad. Sci. USA, 78:3199-3203 (1981); Foster et al., Virchows Arch, 394:27-293 (1982); Ellis et al., Histopathology, 8:501-516 (1984); Ashall et al., Lancet, 2:1-11 (1982)] which were determined also to recognize a mucin-like glycoprotein. These monoclonal antibodies were found to recognize such mucin-like glycoproteins that vary in mass from approximately 250,000 daltons to over one million daltons, depending on the immunogen preparation. Shimizu et al., Biochem J., 233:725-730 (1986).

In biochemical studies of the large molecular weight mucin-like glycoproteins of the human milk fat globule membrane, it was suggested that these glycoproteins are complexes consisting of at least three distinct components which may represent at least three distinct molecular entities. Shimizu et al., Biochem J., 233:725-730 (1986). Thus, the mucin-like glycoproteins of the human milk fat globule membrane have been shown to be large molecular complexes which, due to their size, can be expected to have a myriad of epitopes. Monoclonal antibodies have been developed which bind to mucin-like glycoproteins of normal breast epithelial cells and malignant breast cells such as the Mc5 monoclonal antibody described in Ceriani et al., Somatic 5 Cell Genetics, 9:415-427 (1983). Additionally, a monoclonal antibody D-274, specific to guinea pig milk fat globule membrane, was used to determine the distribution of mucin-like glycoproteins of greater than 400,000 daltons in both benign fibrocystic disease and infiltrating duct carcinoma of the human breast. Greenwalt et al., Am. J. Pathol., 118:351-359 (1985).

Prior art monoclonal antibodies have been developed that will bind to normal human breast epithelial cells, to breast carcinoma cells, as well as, to some epithelial cells of other tissues. It would be highly advantageous in tumor cell identification, diagnosis, prognosis and therapy to provide a monoclonal antibody which will bind to a unique epitope that is expressed on the surface of normal breast epithelial cells and on the surface and/or in the cytoplasm of human breast carcinoma cells and some carcinoma cells of other tissues.

SUMMARY OF THE INVENTION

A monoclonal antibody which binds to a novel mucin-like glycoprotein antigen on the surface and/or in the cytoplasm of human breast carcinoma cells and carcinoma cells of other adenocarcinomas and on the surface of normal human breast epithelial cells. The monoclonal antibody does not bind to normal tissue of the heart, liver, ovary, spleen, testis, brain, prostate, thyroid, bladder, colon, esophogus and uterus.

The antigen recognized by the monoclonal antibody is termed BrE2 and is characterized as having a high molecular weight which may exceed 400,000 daltons. The specificity of the BrE2 monoclonal antibody enables advantageous differentiation studies, prognostic, diagnostic and possible therapeutic applications in the evaluation and treatment of breast carcinomas.

The BrE2 monoclonal antibody was developed using normal delipidated human milk fat globule as the immunizing agent.

DESCRIPTION OF THE PREFERRED EMBODIMENT

Development of the monoclonal antibody embodying the invention utilized standard procedures generally described by Kohler and Milstein, Nature, 256:495-497 (1975). The host animal was immunized with whole delipidated human milk fat globule (HMFG) prepared as described in Ceriani et al., Proc. Natl. Acad. Sci. USA, 74:582-586 (1977). The host animals were New Zealand black (NZB) mice and after a suitable period of incubation, the murine spleen cells were harvested.

The harvested spleen cells thereafter were fused with P3-X63-Ag8.653 mouse myeloma using well known polyethylene glycol techniques. The screening for identifying the hybridoma or hybrid cell line which produced the monoclonal antibody of the invention was done using both a solid phase radioimmuno-plate binding assay and an ELISA assay using the HMFG and components of HMFG in wells of a microtiter plate as described in Ceriani et al., Somatic Cell Genetics, 9:415-427 (1983). Thereafter, the wells positive for HMFG were screened on cell lines from cervical carcinoma and colon carcinoma. A monoclonal antibody was identified which did not stain these latter carcinoma cell lines and the hybrid cell which produced that antibody was isolated. This monoclonal antibody is identified herein as anti-BrE2. The molecular weight or Mr of the antigen identified by the BrE2 monoclonal antibody was determined by Western Blot test as described by Towbin et al., Proc. Natl. Acad. Sci. USA, 76:4350-4354 (1979) and solid-phase binding assay as described by Ceriani et al., Monoclonal Antibodies and Functional Cell Lines, Plenum Press, New York, 398-402 (1984).

In the Western blot test, the HMFG was separated by a 7% polyacrylamide gel electrophoresis and then electroblotted to nitrocellulose paper. The nitrocellulose was cut into strips and the strips incubated. High molecular weight standards were simultaneously run on parallel lanes of the gel.

In the solid-phase binding assay, HMFG was electrophoresed on 7% polyacrylamide gel as described by Laemmli VK, Nature, 227:680 (1970). The gel lane was sliced into fractions, the slices eluted, and the eluate dried onto microtiter plates. Binding of monoclonal antibody was tested by a radioimmunobinding assay technique. When the HMFG was electrophoresed, in both the Western blot test and the solid-phase binding assay, the monoclonal antibody BrE2 identified a material found only at the origin of the polyacrylamide gel. Thus, the mucin-like glycoprotein antigen identified by the monoclonal antibody BrE2 remained at the origin and did not penetrate the polyacrylamide gel. The HMFG then was electrophoresed on less than 7% polyacrylamide gel using the solid-phase binding assay previously described. The molecular weight of the mucin-like glycoprotein antigen of HMFG identified by the monoclonal antibody BrE2 was then calculated using high molecular weight standards. The molecular weight of this antigen was estimated to exceed 400,000 daltons. Studies were conducted between the BrE2 and the Mc5 monoclonal antibodies to study the competition between them for the glycoprotein antigen. The monoclonal antibody BrE2 was found not to compete for binding with the same epitope to which the Mc5 monoclonal antibody bound.

In assays of body fluids which contained breast carcinoma cells or molecules using the BrE2 monoclonal antibody, we determined that in addition to binding to a molecular complex greater than 400,000 daltons, there also occurred binding to a glycoprotein molecular entity which exhibited a molecular weight of less than 400,000 daltons. It is postulated that the high molecular weight mucin-like glycoprotein antigen to which the BrE2 monoclonal antibody bound had become denatured in the body fluid such as to fragmentize. It appeared that the BrE2 monoclonal antibody recognized a common epitope on the high molecular weight antigen and the molecular entity or fragment which would explain the phenomenon. Thus, although the BrE2 monoclonal antibody binds specifically to the high molecular weight antigen exceeding 400,000 daltons, it also can bind to a common epitope of the antigen found on such a molecular entity. This is possible since the high molecular weight antigen appears to be a complex of molecular entities.

The BrE2 monoclonal antibody isotype was determined using a mouse immunoglobulin kit to be IgG1.

The BrE2 monoclonal antibody was tested extensively for binding to histological sections in order to further characterize its tissue specificity. Standard immunoperoxidase assay procedures were used for binding to histological sections of normal and cancerous human tissue. The tissues were prepared in the form of multi-tumor tissue blocks as described by Batifora, H., Lab Invest., 55:244.248 (1986). Each tissue block was prepared from a collection of strips of fixed tissues by wrapping the tissues in peritoneal membrane or intestine and embedding in paraffin. The blocks then were sliced in preparation for the binding studies. In this manner, a large number of different tissues were assessed with a single staining.

The breast block used to characterize the BrE2 monoclonal antibody contained 21 different specimens from normal breast, 22 adenomas, and 33 breast carcinomas. The BrE2 monoclonal antibody stained all test tissues tested.

The BrE2 monoclonal antibody was also tested on a large panel of different normal and tumor tissues other than normal breast tissue or breast carcinoma. The BrE2 monoclonal antibody bound to normal tissues of the alveolar lining cells of the lung, the distal convoluted tubules of the kidney, the apical regions of the acinar epithelium of the pancreas and the entire thickness of the mucosa of the stomach. The BrE2 monoclonal antibody did not bind to normal tissue of the heart liver, spleen ovary, testis, brain, prostate, thyroid, bladder, colon, esophagus and uterus.

The BrE2 monoclonal antibody bound to several adenocarcinomas of other than breast origin. A combination of apical membrane staining and cytoplasmic staining was noticed in the majority of tumors. The BrE2 monoclonal antibody bound to a majority of adenocarcinomas of the lung and ovary.

A sample of the hybrid cell line capable of producing BrE2 monoclonal antibodies is on deposit with the American Type Culture Collection, 12301 Parklawn Drive, Rockville, Md., 20852 and is assigned A.T.C.C. No. HB 9795., said hybrid cell line having been shipped to the American Type Culture Collection on Aug. 16, 1988 and received on August 17, 1988.

The BrE2 monoclonal antibody is unique because of its exceptional specificity for a mucin-like glycoprotein complex of very high molecular weight present on the surface of normal breast epithelial cells and on the surface or in the cytoplasm of breast carcinoma cells and which expresses no specificity for normal tissue of the heart, liver, ovary, spleen, testis, brain, prostate, thyroid, bladder, colon, esophagus and uterus. Consequently the BrE2 monoclonal antibody can be useful in several ways. It can be used as one component of a "cocktail" of anti-breast antibodies, each having different binding specificities. Since the cocktail is composed of monoclonal antibodies having different cell and tissue specificity, it is useful for breast carcinoma diagnosis and therapy, as well as, studying cell differentiation and cell-type specificity. For example, the monoclonal antibody can be tagged with a detectable label such as a dye or fluorescent molecules or a radioactive tracer for tumor imaging. A suitable tracer would be Iodine[131], Indium[111] or Technetium[99]. The monoclonal antibody can be used therapeutically both in conjugated and unconjugated forms in a cocktail of several monoclonal antibodies or separately. Suitable conjugates for the BrE2 monoclonal antibody include chemotherapeutic drugs, toxins or radioisotopes. Radioisotopes, such as Iodine[131], can be conjugated directly to the BrE2 monoclonal antibody. Radioisotopes such as Indium[111] or Yttrium[90] can be conjugated indirectly to the BrE2 monoclonal antibody through the use of chelators or by other known means. The conjugated or unconjugated BrE2 monoclonal antibody may be administered in a cocktail of monoclonal antibodies or in separate dose form.

Immunoassay in which microspheres are utilized in conjunction with antigens or antibodies coated thereon and suitably tagged or labelled, can be employed for in vitro diagnostic applications with the BrE2 monoclonal antibody. Typically, a biological sample of human carcinoma cells such as breast carcinoma cells thought to contain the BrE2 antigen, or substances derived from the carcinoma cells which substances are thought to contain the BRE2 antigen, are contacted with labelled BrE2 monoclonal antibody. The labelled antibody and antigen are contacted for a length of time and under conditions sufficient for the formation of an immunological complex between the antibody and the antigen. The immunological complex is separated from the reaction system and assayed to determine the presence the BrE2 antigen. The labels or tags may be varied as discussed herein and known in the art. For in vitro applications, the BrE2 monoclonal antibody may be provided in an assay kit accompanied by other ingredients for completing the assay of a biological sample according to assay instructions in insert literature, for instance. The same may be feasible for in vivo applications, both for diagnostic and therapeutic uses. The assay may be used with flow cytometric procedures to study cell differentiation and cell specificity. The BrE2 monoclonal antibody also may be used as a prognostic tool in the histopathology of tumors to determine, for example, the outcome of a malignancy, the likelihood of dissemination of a malignancy or the stage of the malignancy. These examples of in vitro and in vivo applications should not be deemed to exclude other applications of the use of the BrE2 monoclonal antibody.

We claim:

1. A cell line developed by hybridoma technique which produces a monoclonal antibody specific to a unique antigenic determinant present on the surface and/or in the cytoplasm of human breast carcinoma cells, cells of other adenocarcinomas and on the surface of normal human breast epithelial cells, a sample of said cell line being on deposit with the A.T.C.C., Deposit No. HB 9795.

2. The cell line according to claim 1 wherein said monoclonal antibody producing cells are hybridoma cells produced from mouse spleen cells immunized with delipidated human milk fat globule.

3. The cell line according to claim 1 in which said monoclonal antibody producing cells are hybridoma cells produced from mouse spleen cells immunized with normal whole human milk fat globule membrane.

4. The cell line according t o claim 1 in which said monoclonal antibody producing cells are hybridoma cells produced from mouse spleen cells immunized with normal human milk fat globule components.

5. The cell line according to claim 1 in which said antigen is undetectable by said monoclonal antibody on normal tissue cells selected from the group consisting of the heart, liver, spleen, ovary, testis, brain, prostate, thyroid, bladder, colon, esophagus and uterus.

6. The cell line according to claim 5 in which said monoclonal antibody binds to normal epithelial cells of the alveolar lining cells selected from the group consisting of the lung, the distal convoluted tubules of the kidney, the acinar epithelium of the pancreas, and the mucosa of the stomach.

7. The cell line according to claim 1 in which said monoclonal antibody binds to epithelial cells of adenocarcinomas selected from the group consisting of the breast, lung, and ovary.

8. A monoclonal antibody produced by the hybridoma cell line sample on deposit with the American Type Culture Collection and assigned A.T.C.C. deposit number 9795.

* * * * *

UNITED STATES PATENT AND TRADEMARK OFFICE
CERTIFICATE OF CORRECTION

PATENT NO. : 5,077,220

DATED : December 31, 1991

INVENTOR(S) : Roberto L. Ceriani and Jerry A. Peterson

It is certified that error appears in the above-identified patent and that said Letters Patent is hereby corrected as shown below:

Column 1, line 39, cancel "394:27-293" and insert

--394:279-293--.

Column 1, line 61, cancel "5".

Column 3, line 32, after "that" insert --,--.

Column 4, line 13, after "heart" insert --,--.

Column 4, line 68, cancel "BRE2" and insert

--BrE2--.

Signed and Sealed this

Twentieth Day of April, 1993

Attest:

MICHAEL K. KIRK

*Attesting Officer*    *Acting Commissioner of Patents and Trademarks*